(12) United States Patent
Nath

(10) Patent No.: US 8,308,330 B2
(45) Date of Patent: Nov. 13, 2012

(54) BACKLIGHT APPARATUS WITH REMOTE LIGHT SOURCE

(76) Inventor: Günther Nath, Deisenhofen (DE)

( * ) Notice: Subject to any disclaimer, the term of this patent is extended or adjusted under 35 U.S.C. 154(b) by 515 days.

(21) Appl. No.: 12/475,666

(22) Filed: Jun. 1, 2009

(65) Prior Publication Data

US 2009/0294693 A1 Dec. 3, 2009

(30) Foreign Application Priority Data

Jun. 2, 2008 (DE) .......................... 10 2008 026 288

(51) Int. Cl.
*G01D 11/28* (2006.01)
(52) U.S. Cl. ......... 362/560; 362/97.4; 362/84; 362/293; 362/632
(58) Field of Classification Search ................... 362/559, 362/560, 97.1, 97.4, 84, 293, 632, 602, 604
See application file for complete search history.

(56) References Cited

U.S. PATENT DOCUMENTS

| | | | | |
|---|---|---|---|---|
| 838,167 | A * | 12/1906 | Clawson | 396/602 |
| 919,245 | A * | 4/1909 | Roberts | 362/97.4 |
| 1,113,263 | A * | 10/1914 | Ulrich | 108/23 |
| 1,163,647 | A * | 12/1915 | Dick | 101/128.4 |
| 1,320,537 | A * | 11/1919 | Dimond | 362/99 |
| 1,572,160 | A * | 2/1926 | Robbins | 362/145 |
| 1,610,171 | A * | 12/1926 | Sheppard | 250/488.1 |
| 2,134,650 | A * | 10/1938 | Williams | 356/238.1 |
| 2,407,596 | A * | 9/1946 | Wirshing et al. | 430/139 |
| 2,742,321 | A * | 4/1956 | Mina et al. | 222/192 |
| 3,596,095 | A * | 7/1971 | Leach | 250/461.1 |
| 4,835,661 | A * | 5/1989 | Fogelberg et al. | 362/97.1 |
| 4,933,816 | A * | 6/1990 | Hug et al. | 362/551 |
| 5,504,661 | A * | 4/1996 | Szpak | 362/30 |
| 5,515,162 | A * | 5/1996 | Vezard et al. | 356/318 |
| 5,832,159 | A * | 11/1998 | Davis | 385/53 |
| 6,068,383 | A * | 5/2000 | Robertson et al. | 362/84 |
| 6,120,160 | A * | 9/2000 | Nakagawa | 362/97.1 |
| 6,425,674 | B1 * | 7/2002 | Su | 362/629 |
| 7,431,467 | B2 * | 10/2008 | Nath et al. | 362/20 |
| 7,745,102 | B2 * | 6/2010 | Fedynyshyn et al. | 430/322 |
| 2005/0019603 | A1 * | 1/2005 | Kathirgamanathan | 428/690 |
| 2005/0161644 | A1 * | 7/2005 | Zhang et al. | 252/582 |
| 2006/0154188 | A1 * | 7/2006 | Hirayama et al. | 430/338 |
| 2008/0311530 | A1 * | 12/2008 | Allen et al. | 430/327 |

* cited by examiner

*Primary Examiner* — Ismael Negron
(74) *Attorney, Agent, or Firm* — Barnes & Thornburg LLP

(57) ABSTRACT

An apparatus for optical examination of documents. The apparatus includes a light source, a plurality of panels which are exchangeable with each other, a viewing unit having a window formed by at least one of the plurality of exchangeable panels through which window light emitted from the light source exits for examination of documents by an observer. Further included is a coupling unit configured to supply the light emitted from the light source into the viewing unit. The light source and the viewing unit are coupled together by a light guide and the light guide is adapted to supply the light from the light source to the coupling unit. At least one of the plurality of exchangeable panels is a fluorescent panel including a fluorescent substance. The fluorescent panel is fluorescent in the yellow-red-infrared wavelength range when being illuminated with light in the ultraviolet-blue-green wavelength range.

10 Claims, 10 Drawing Sheets

BACKLIGHT APPARATUS WITH REMOTE LIGHT SOURCE

BACKGROUND OF THE INVENTION

U.S. Pat. No. 7,431,467 (Title: "Portable Forensic Lighting Device") discloses a cross-section converter for converting a circle-shaped light spot into an elongate rectangular light spot by means of mirrors. The elongate rectangular light spot is useful for detecting shoe prints at a crime scene. The disclosure of this patent document is hereby incorporated by reference.

The light source of the forensic lighting device described in U.S. Pat. No. 7,431,467 is an Hg-lamp having an extremely high pressure of Hg-vapor of about 200 atmospheres ($2 \times 10^7$ Pa). The radiation of this lamp is spread over a spectral range from about 300 nm to 700 nm and is focused into a liquid light guide. The output radiation of the light guide is supplied to the cross-section converter which is a triangular shaped hollow body with metallized inner surfaces. The radiation undergoes multiple reflection in the interior of the reflector cavity and exits through a narrow elongate rectangular window made of acrylic glass. The intensity of the radiation is distributed rather homogeneously across the light output surface. The radiation spreads fan-shaped across the ground and facilitates the detection of weakly pronounced relief structures of shoe prints.

SUMMARY OF THE INVENTION

The present disclosure relates to modifying the conventional cross-section converter for shoe print detection such that it can be used as an apparatus for examination of documents in the light transmission mode. The light source with connected liquid light guide described as the forensic lighting device in U.S. Pat. No. 7,431,467 may still be used as radiation source, so that the apparatus for examination of documents, according to the present disclosure, can be defined as an accessory to the conventional forensic lighting device.

The present disclosure thus relates to, among other things as disclosed herein, an apparatus for optical examination of documents. The apparatus includes a light source, a viewing unit having a window through which light emitted from the light source exits for examination of documents by an observer, and a coupling unit configured to supply the light emitted from the light source into the viewing unit. The window may comprise a fluorescent perylene compound. The present disclosure also relates to a method for optical examination of a document. The method steps include providing a light source; emitting light from the light source into a viewing unit; emitting light from the viewing unit through a window; applying fluid to a document to be viewed; bringing the document into contact with the window such that an observer can examine the document. The fluid may be a fluorated immersion liquid.

The present disclosure deals with transmitting light through, for example, closed envelopes for determining the content, such as, for example, drugs, explosives, money, and texts, or for verifying the validity of personal identity cards, passports and driving licenses in the transmission light mode. By using the forensic lighting device as the light source, light transmission of the documents is possible in ten or more different spectral regions between 300 nm and 700 nm by turning a filter wheel of the forensic lighting device as disclosed in further detail in U.S. Pat. No. 7,431,467.

Document areas of up to the size of DIN A4 can be transilluminated. A super high pressure Hg-lamp, such as a VIP®-lamp or HTV®-lamp or UHP®-lamp, included in the known forensic lighting device, may be used as the light source. The main emission of this lamp, namely about 70% of the total emission, lies in the spectral range from 300 nm to 500 nm, because this type of lamp has presently the highest efficiency rate of all vapor discharge lamps concerning the conversion of electrical into optical power.

For the transmission of light through whitish or brightly colored documents, the strongly blue-colored radiation of the HTV®-lamp, manufactured by the company Osram, provides satisfactory results. Darker-colored documents or envelopes which are often brownish or greyish, may be radiated with longer wavelengths, i.e. red radiation, because it passes better through the darkly pigmented paper material than blue radiation. Since the HTV®-lamp has practically no emission in the red spectral region, the red bandpass filters provide no positive effect in the transillumination of the darker pigmented paper documents.

It has been surprisingly found that the use of a red fluorescent acrylic glass panel as a supporting surface for the documents to be examined leads to a significant improvement of contrast. By doping, for example, acrylic glass with the strongly red fluorescent dye Lumogen®, a dye selected from the group of perylenes, the incident and absorbed blue radiation, generally radiation from the short wavelength main emission range of the HTV®-lamp of the forensic lighting device is in the range between 300 nm and 500 nm, is converted into red radiation in the wavelength region around 630 nm. The quantum yield of the blue absorbed radiation is nearly 100% for the generation of red light quanta from blue absorbed light quanta. Thereby, it is possible to convert a portion of the blue radiation, which is useless for the transillumination of dark colored documents or envelopes, into useful more deeply invading red radiation without the need of using a new alternative radiation source with emission in the red spectral region, such as tungsten-halogen or xenon-lamps. For examination under red light, one simply uses the red fluorescent acrylic glass panel as a supporting surface.

Such acrylic glass panels doped with the dye "Lumogen® red" are available in the market. Typically, they have a thickness of about 3 mm, have coplanar polished surfaces, and attract attention by intensively shining edges in which the red fluorescent light is concentrated. These intensively shining edges can be explained by the light guiding effect of the coplanar panels which are polished on both sides. The internally generated red fluorescent light undergoes total reflection at the material borderline of glass and air.

When using one such colored acrylic glass panel as a document support, one or both of the polished plane surfaces of the panel can be structured by corrugating, roughening, sand blasting, or satinizing to disturb the light guiding mechanism and to get more red emission through the plane surface.

However, it is also possible to use the highly intensive red shining edges as a reading line for the documents by moving the document or the envelope across the shining edge for reading line by line. With this use of the illumination panel, it is advisable to metallize the non-used other shining edges of the panel and the outer surface of the panel facing away from the pumping radiation in order to concentrate as much intensity of red light as possible at the reading edge. The metallization of the outer surface of the fluorescent panel, possibly including a small intermediate air layer, allows for reversing the non-absorbed blue pumping light transmitted through the panel. Thereby, the pumping radiation can be used more efficiently.

A further drastic enhancement of the transparency of the documents under examination can be achieved by spraying or painting one or both surfaces of the documents with an appropriate immersion fluid during the transmission of light. This concept of moistening the documents during the transmission with light is already known. For example, benzine or Trihexane or hexane are used as immersion fluids. However, these known fluids have the disadvantage that they persistently change the documents and destroy them, in the worst case, because they begin to dissolve the material or make it swell. Also, the reactive fluids do not guarantee a fast vaporization without remainder.

An immersion fluid which is ideal for the examination of documents should have the following properties:

1. The fluid should be scentless, physiologically harmless and non-burning.
2. It should be chemically inert and its molecules should not contain reactive groups.
3. It should not have any dissolving properties.
4. The latent vaporization heat should be negligible, i.e. it should be practically zero, the molecules should not have any dipole moments, and a paper immersed with the fluid should dry completely within a few minutes without any remaining traces of swelling, odor or other changes and remainders.
5. The boiling temperature should lie between 60° C. and 150° C.

Perfluorated or at least partially fluorated organic fluids, whose molecules consist exclusively of the elements C and F, or C, F and H, or C, F and O, or C, F, H and O, have turned out to be ideal immersion fluids. They should have only single bonds of the type C—F, C—H or C—O, i.e. no double bonds. Among these fluids, the perfluorated ones may be advantageous. As an example of such fluids perfluorated compounds are named, e.g. primary compounds having eight carbon atoms:

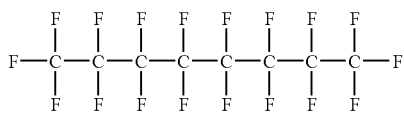

When spraying the document under examination with such a fluid during the transmission with light, the document becomes highly transparent for about 2 minutes, so that there is enough time for photographical documentation. By pressing a transparent plane panel onto the transilluminated envelope, the recognition and the identification of the writing in a letter enclosed within the envelope can be facilitated. Moreover, the recognition of writings and other markings can be improved by using a magnifying glass of 4 to 10-fold magnification.

Other aspects of the present disclosure will become apparent from the following descriptions when considered in conjunction with the accompanying drawings.

DETAILED DESCRIPTION OF THE DRAWINGS

Figure 1:
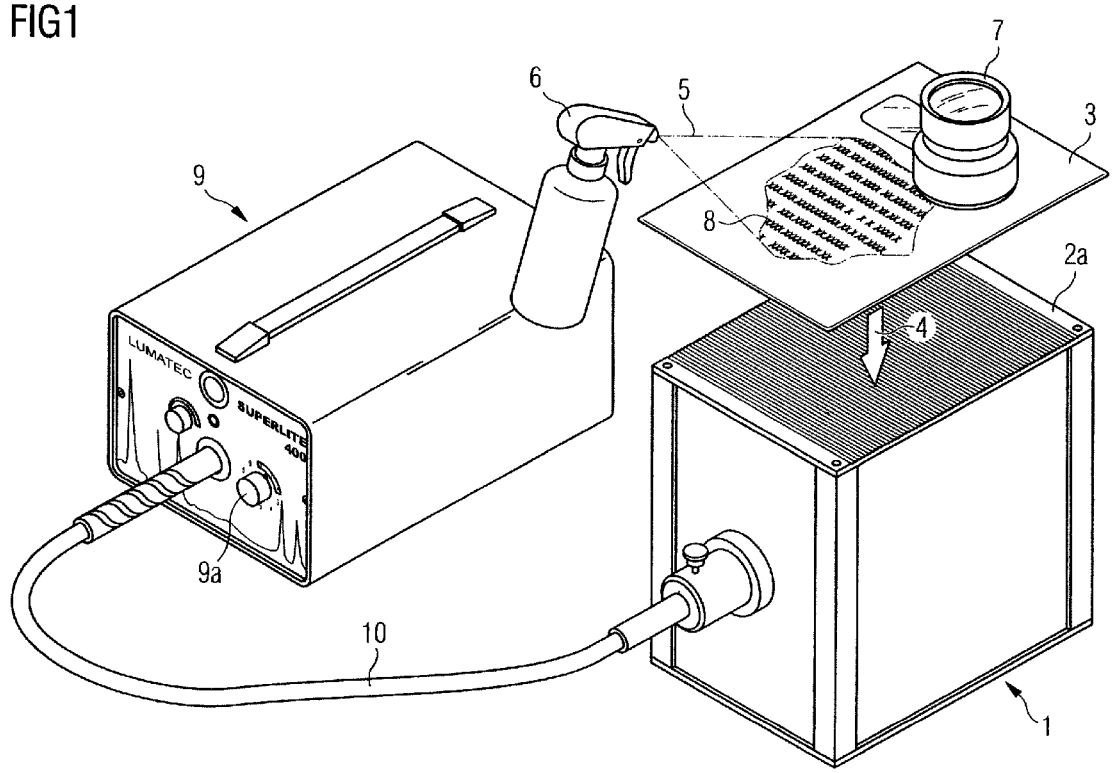
FIG. 1 shows a perspective view of an apparatus for optical examination of documents, according to a first embodiment of the present disclosure, showing a viewing unit in the form of a mirror box and a window in the form of a supporting panel.

FIG. 1 shows the complete setup of an embodiment of an apparatus for optical examination of documents comprising a light source, which may be an external light source (9), a liquid light guide (10), and a box (1), which may be a mirrored box (1A), metallized on the inside and having a supporting surface (4), which surface (4) may have the size of a DIN A5 or DIN A4 format. The light source (9) includes a radiation source which may be, for example, a HTV®-lamp in the electrical power region from about 100 W to 250 W. The radiation of the HTV®-lamp is focused within the light source (9) by a reflector into a liquid light guide (10) and is emitted into the inner lumen of the box, or mirror box (1). In the white light region from 300 nm, to 700 nm, a radiation power of about 15 W can be provided in the inside of the mirror box (1).

A fluorescent panel. or supporting panel (2a), for example, is an acrylic glass panel doped with "Lumogen®red". The surface of the panel (2a) is smooth or has a corrugated structure. The document, e.g. an envelope (3), which may, for example, he white and/or open and/or closed and/or be brown pigmented, as in this case, is put onto the supporting panel (2a). With full white illumination inside the mirror box (1), a writing, or written document (8) of a letter inside the closed envelope (3) can be read in the reddish light of the fluorescent panel (2a).

The readability of the writing (8) can be substantially improved by spraying the envelope (3) with a perfluorated liquid, or fluorescent immersion fluid, (5) from a spraying bottle (6) and by placing a magnifying glass (7) thereon.

When turning a turning knob (9a) on light source (9), a filter wheel inside the light source (9) is rotated. The filter wheel includes ten or even more bandpass filters in the spectral region between 300 nm and 700 nm. The use of the narrow bandpass filters for light transmission is of particular relevance for the validation of identity cards, passports or driving licenses. In this respect, UV-light is of particular importance.

Figure 2:
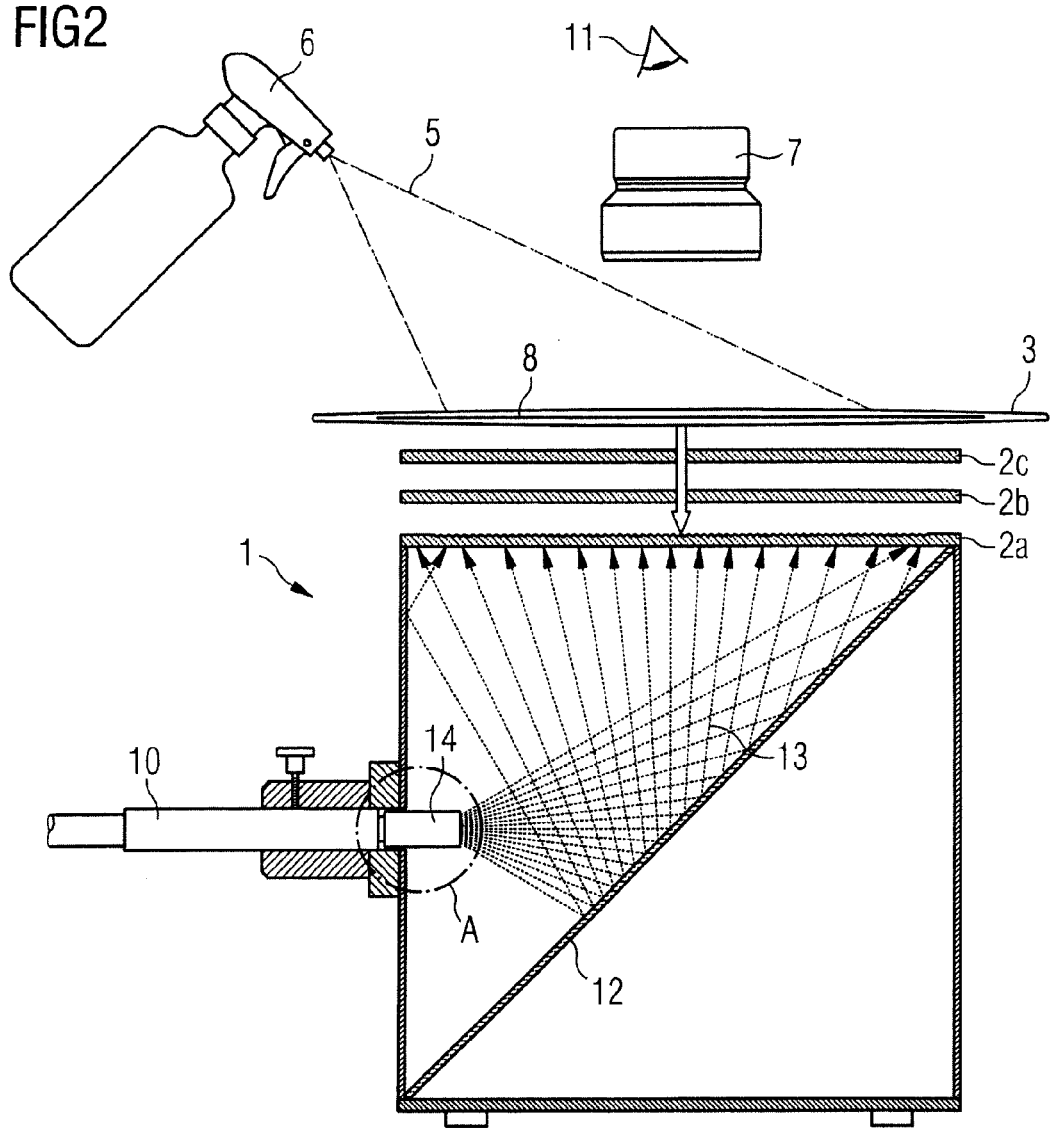
FIG. 2 shows a cross-sectional view of the first embodiment of FIG. 1, in which three alternative supporting panels are shown.

FIG. 2 shows the inside of the mirror box (1) in cross-section. A liquid light guide (10) emits radiation (13) into the inner volume of the mirror box (1). The radiation (13) impinges onto a mirror, or mirror panel, (12) which is disposed obliquely, for example, and which may, for example, be a high reflective aluminium plate. The mirror (12) reflects the radiation to one of the supporting panels (2a, 2b, 2c). which supporting panels may be transparent or fluorescent. In FIG. 2, the three supporting panels 2a, 2b, 2c are shown to illustrate their exchangeability. Indeed, only one panel (2a, 2b or 2c) is used at once in the above-noted embodiment.

The side walls and the base panel of the mirror box (1) are also metallized highly-reflective in the inner volume, wherein the obliquely disposed mirror panel (12) may also be omitted. In either case, the complete radiation is transmitted through the transparent or fluorescent supporting panel (2a, 2b, 2c) to the outside.

Figure 3:
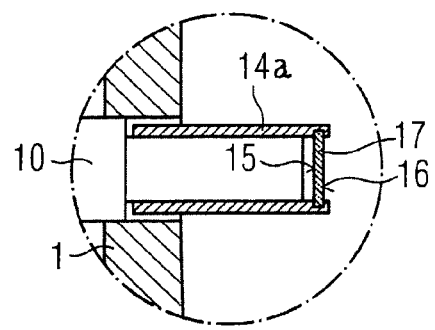
FIG. 3 shows the enlarged part A of a light output from FIG. 2.

A light output part (14) of the liquid light guide (10) is shown in greater detail in FIG. 3. Before entering the inner volume of the mirror box (1), the radiation emitted from the light guide (10) impinges on a small diffusor plate (17) made of heat resistant, UV-transparent glass roughened on its two surfaces (15, 16). Thereby, it is achieved that the radiation leaving the light guide (10), with an angle of divergence of only about 60°, becomes highly divergent such that the area of the panel (2a, 2b, 2c) onto which the documents are pressed can be illuminated sufficiently homogeneously.

A diffusor plate (17), which may be roughened only on one side, is bordered into a sleeve (14a) which is in turn put onto the light output window of the light guide (10). In case the one side roughening of the diffusor (17) is already sufficient for the homogeneous illumination of the document, the diffusor plate (17) can also be omitted and the light output surface, which is made of silica glass, of the liquid light guide (10) itself can be roughened.

The light output surface can be roughened on only one side or not at all, if the mirror box (1) is of smaller dimensions having a document support in the size of personal identity cards, driving licenses or bank notes. The dimensions of the mirror box (1) should not be larger than necessary, because the intensity of the radiation at disposal for the transillumination of the documents can then always be maximum.

FIG. 2 shows, for example, three different possibilities for the panel (2a, 2b, 2c) for supporting documents. One panel (2a) includes an acrylic glass panel of 3 mm thickness whose surface is structured at least on one side. The size of the panel (2a) may be 150 mm×200 mm, for instance. The acrylic glass panel (2a) is doped with the dye "Lumogen® red" which is a red fluorescent dye with excitation or absorption in the wavelength region from about 300 nm to 500 nm. Instead of "Lumogen® red", one may also use "Lumogen® orange" or "Lumogen® yellow".

Instead of acrylic glass, some other transparent material may be used for the supporting panel, such as glass, polycarbonate or some other transparent plastic material. The structuring of one of the two surfaces of the panel (2a) can also be omitted, particularly in case of higher dopings with the dye, if the edges no longer shine. The fluorescent dye can also be applied in the form of a thin layer onto the lower side of the transparent supporting plate, such a panel (2a), also in the form of a powder coating. Instead of Lumogen® other fluorescent dyes, such as rhodamines, metal oxides or oxides of the transition metals can be used.

The surface corrugation, roughening or satinizing of the panel (2a) is such that a greater portion of the fluorescent radiation is obtained for the transillumination. That is because a higher portion of the fluorescent radiation is concentrated in the edges of the panel. Therefore, it is advantageous to metallize these four shining edges, so that the concentrated fluorescent radiation impinging thereon is reflected into the inner volume of the panel (2a). The structuring of the surface of the fluorescent panel (2a) can be effected by corrugating, sandblasting or satinizing of one or both sides.

The supporting panel (2b) is one example for a non-fluorescent panel. It is completely transparent over the complete spectral region, i.e. in the spectral region from 300 nm to 700 nm. UV-transparent acrylic glass having a thickness of 3 mm is very suitable. However, a glass panel made of borosilicate glass can also be used, for example.

The non-fluorescent transparent supporting panel (2b) is used for the transillumination of non-pigmented white documents, such as a white envelope (3) containing written document (8) therein, for example. An observer (11) can substantially facilitate the recognition of details, as already described by setting thereon magnifying glass (7) and by using the fluorated immersion fluid (5) applied by the spraying bottle (6).

Figure 4:
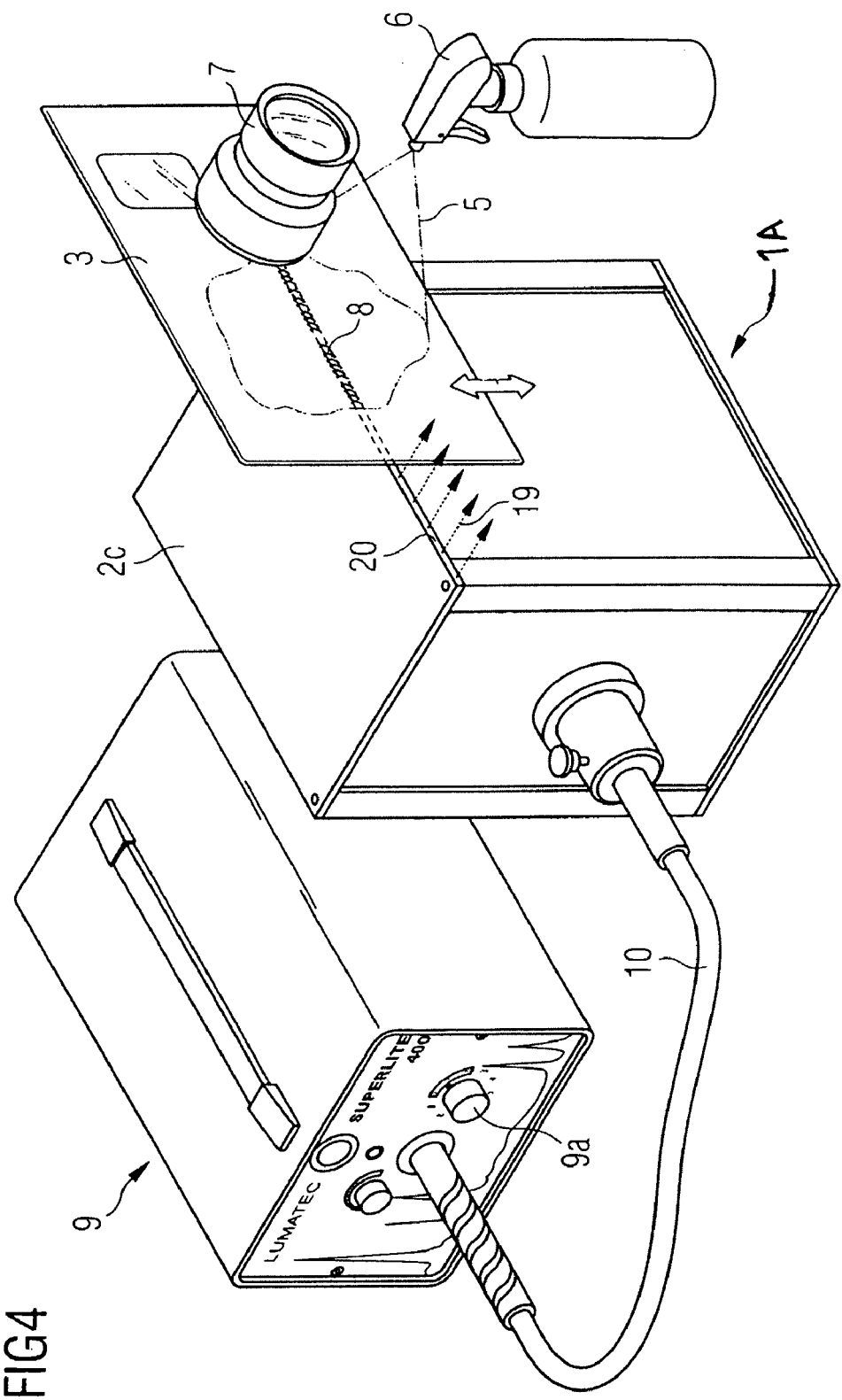
FIG. 4 shows an apparatus for optical examination of documents, similar to the first embodiment of FIG. 1, wherein the supporting panel is changed.

A third alternative supporting panel (2c) is a fluorescent panel, as well as being an acrylic glass panel, as the first panel (2a). However, only one of the intensively shining edges of this panel (2c) is used for reading letters with dark pigmentation. This is shown in further detail in FIG. 4, which shows a transillumination setup in which an extremely bright shining edge (20) of the acrylic glass panel (2c) doped with Lumogen® is used as a reading line. All other edge surfaces and the outer surfaces of the panel (2c) are metallized, so that a maximum intensity of fluorescent radiation (19) emanating from the reading edge (20) is obtained.

The closed envelope (3), with the written document lying therein, is moved across the shining edge (20), so that the written document (8) can be read line by line. The shining edge (20) can also be chamfered and polished so that a reading line of a higher width is obtained. The thickness of the fluorescent panel (2c) may be in the range of 2 to 10 mm. The magnifying glass (7) and the immersion fluid (5) can be used in this setup in a similar way to that of FIG. 1.

In an alternative embodiment, the mirror box (1) having the red fluorescent supporting panel (2a) receives the transillumination irradiation not from an external light source via a light guide but contains itself the illumination source in the form of one or more HTV®-lamps. Instead of the HTV®-lamps, other irradiation sources of poor red light, such as Hg low pressure lamps, can be used, such as energy saving lamps or tungsten-halogen-lamps, to be contained in the mirror box (1). The red fluorescent supporting panel (2a) emphasizes the red light portion which is important for the transillumination.

Figure 5:
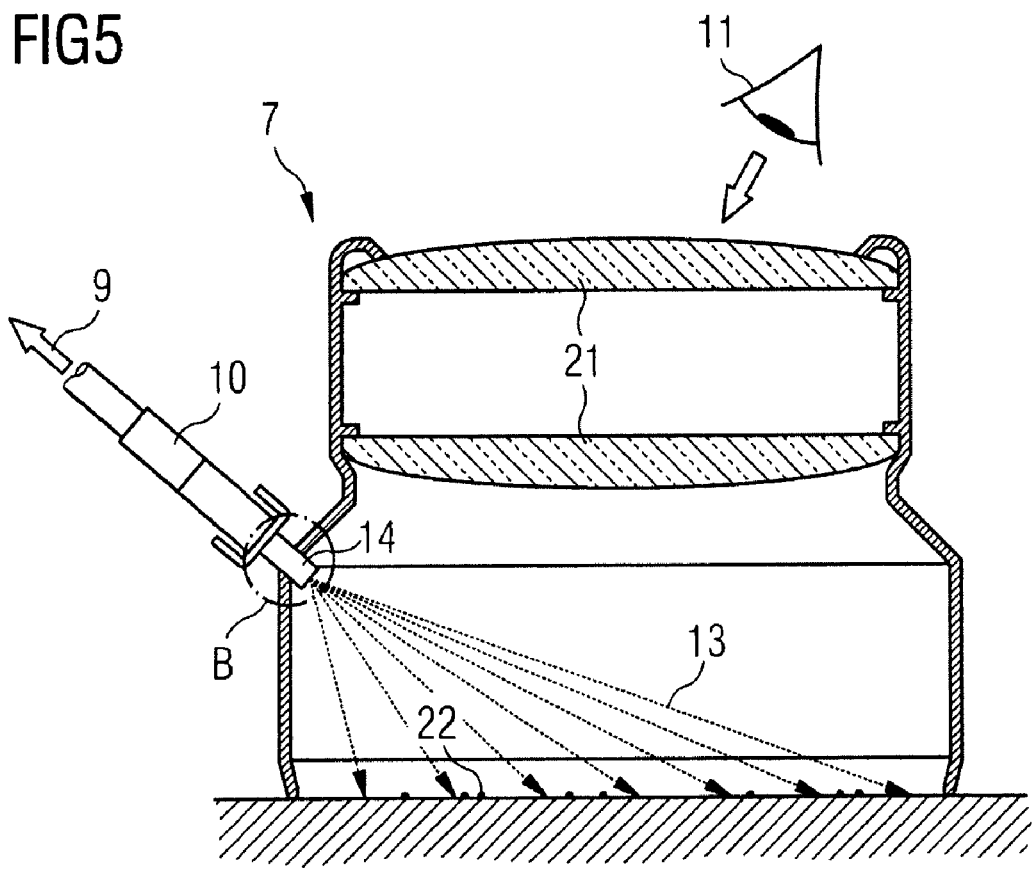
FIG. 5 shows a cross-sectional view of an apparatus for optical examination of documents, according to a second embodiment of the present disclosure, showing a viewing unit in the form of a light active magnifying glass and a window in the form of two lenses.

FIG. 5 shows an even more detailed view of the magnifying glass (7) belonging to an optical examination apparatus, according to the present disclosure. The magnifying glass (7) includes two lenses (21) and is set onto the document (22) which is illuminated from below for the improved recognition of details. The tube-shaped outer mount of the magnifying glass (7) should be made of a material which is not light transmitting, i.e. black, so that the environmental daylight cannot disturb the contrast during the observation. Otherwise, the observation room would have to be darkened. If the magnifying effect of the magnifying glass (7) is not needed, one can simply set a black elongate tube onto the document (22), which is not shown, and which could be seen as an "artificial dark room". This obviates the inconvenience of darkening the outer surrounding.

Figure 6:
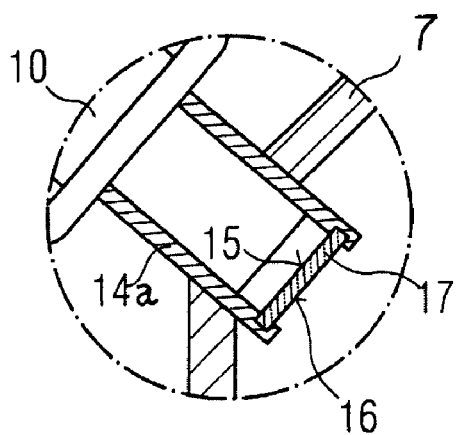
FIG. 6 shows an enlarged part B of a light output from FIG. 5.

The observation magnifying lens (21) itself can have a light active function according to the embodiment shown in FIG. 5. In this case, the inside of the magnifying glass (7) is filled with the radiation (13) which generates incident light for the document (22) in addition to the transmitted light of the mirror box (1). A combined two-sided illumination of a document (22) in this manner can be useful, for example, when looking for fluorescent markers on bank notes with UV-light. A light active magnifying glass can, for example, be realized with a second external light source (not shown). The radiation from the second light source is supplied in a similar way as for the mirror box (1), such as shown in FIGS. 2 and 3, via a liquid light guide (10) into the inner volume of the magnifying glass (7). Analogously to the mirror box (1), FIG. 6 shows that for the magnifying glass (7) as well the output radiation of the light guide (10) can be made homogeneous and highly divergent by disposing a small diffusor plate (17) at the light output end of a sleeve (14a), wherein the plate (17) is roughened on both sides (15, 16) and is UV transmitting.

In this way, the light active magnifying glass (7) can operate with different spectral regions by a turning of the filter wheel (9a) within the light source (9), as suggested in FIG. 1. When viewing with fluorescence, an optical longpass filter, which is not shown, can be set onto the magnifying glass (7). The longpass filter stops the excitation radiation of short wavelengths and transmits the fluorescent radiation of long wavelengths. For reasons of completeness, it is mentioned that the light active magnifying glass (7), described above, is also helpful for making visible minimally pronounced traces at a crime scene, such as finger traces or body fluids, fibers or skin particles, both in white light and fluorescent viewing.

Figure 7:
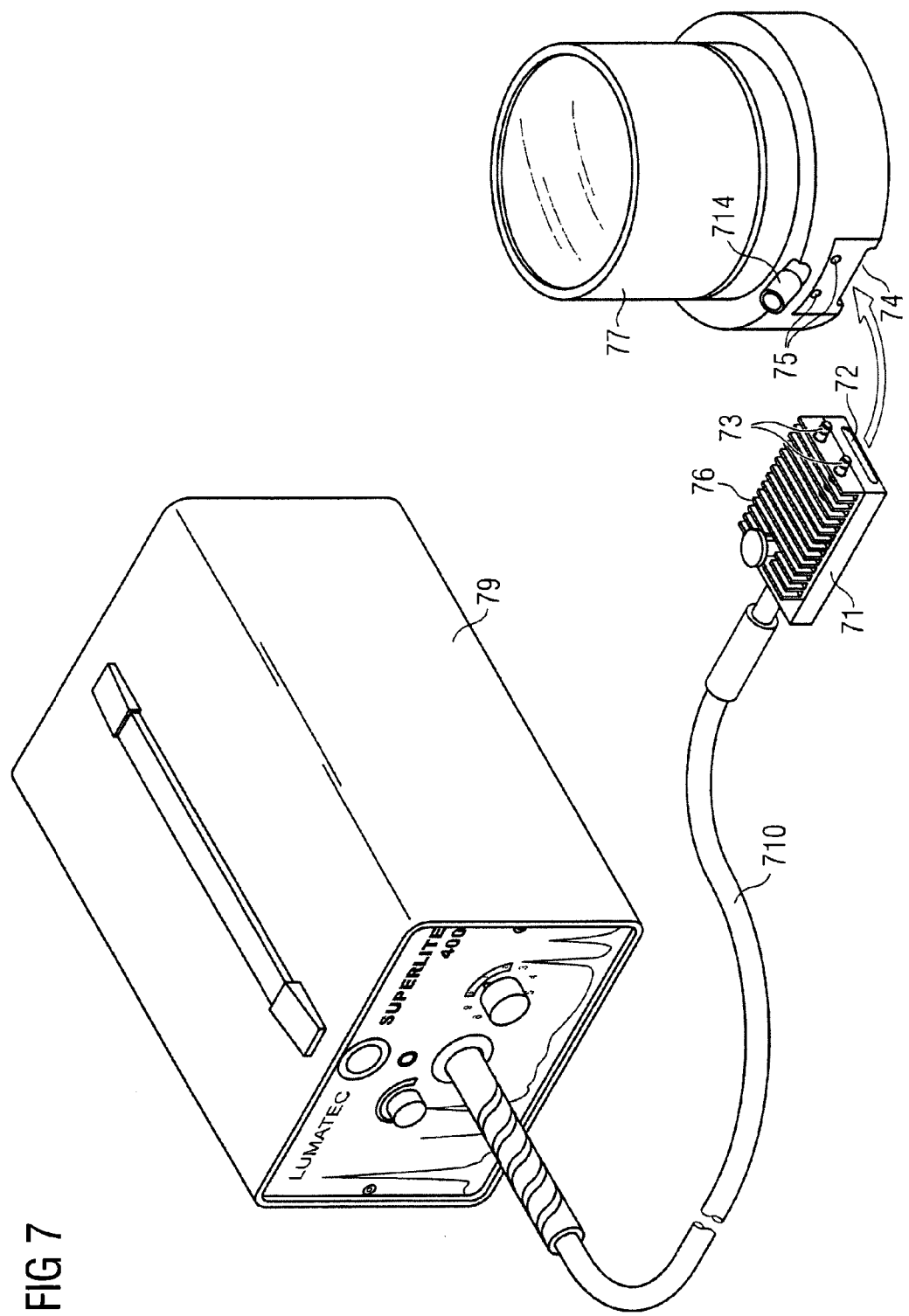
FIG. 7 shows a perspective view of an apparatus for optical examination of documents, according to a third embodiment of the present disclosure, showing a viewing unit in the form of a light active magnifying glass and a window in the form of two lenses.
Figure 8:
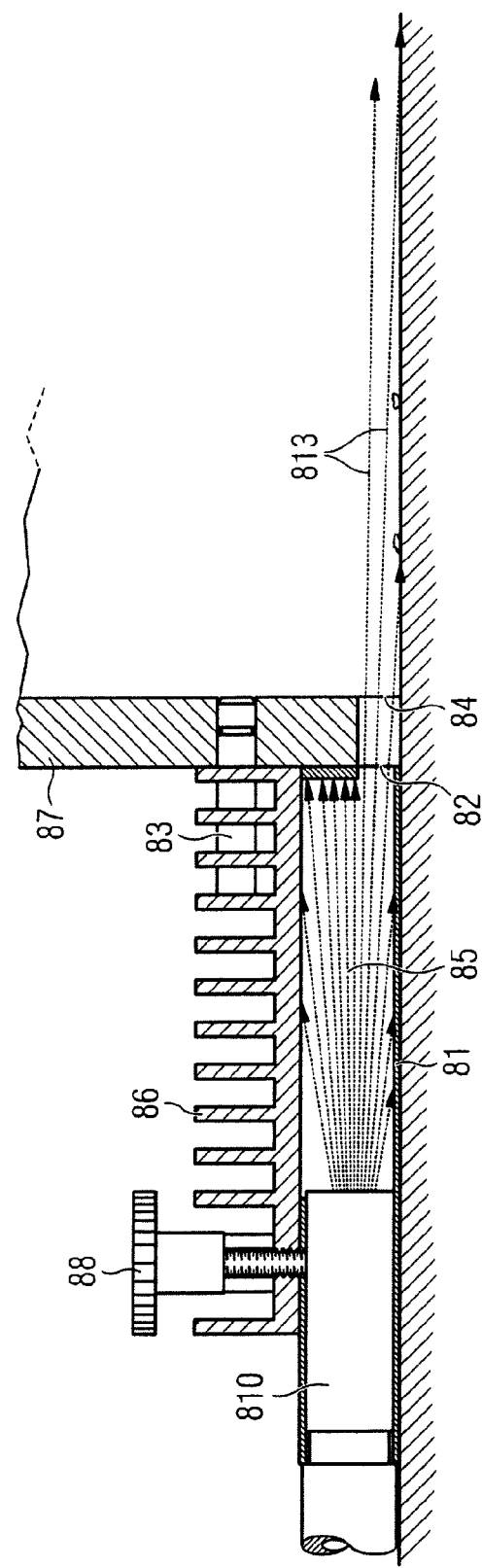
FIG. 8 shows a cross-sectional view of a portion of the third embodiment of FIG. 7.

FIGS. 7 and 8 show another embodiment, according to the present disclosure. This embodiment is a so-called mousehole diaphragm (71) coupled to the lamp. It generates a two-dimensional light fan which illuminates an observing plane of magnifying glass (77) tangentially grazing. Thereby, it distinctively emphasizes the smallest non-regularities or relief structures on the surface of a document under examination in addition to the transmitted light method. A typical application example are written lines pressed through paper.

FIG. 7 shows an overview setup including light source (79), light guide (710), diaphragm (71) with a horizontally slit-shaped mousehole opening (72), cooling ribs (76) and connecting pins (73). With the connecting pins (73), the diaphragm (71) is coupled to the magnifying glass (77) using corresponding receiving holes (75) and corresponding slit-shaped opening (74) being approximately congruent to the opening (72). The opening (72) has a width of 25 mm and a height of only 3 mm and is positioned very closely, only a few tenths of a mm, above the base surface of the diaphragm (71). The light guide (710) is fixed by a fixing screw (88). A normal insertion sleeve (714), provided for the light guide (710), remains free in this special viewing mode of grazing light. The position of the light guide (710) can be simply changed depending on a preferred mode of viewing, either with the light incident obliquely from above or grazing.

FIG. 8 shows a sectional view of a diaphragm (81) which is connected to magnifying glass (87) by connecting pins (83). It is shown that light fan (813) includes only a small portion of the radiation bundle emitted from light guide (810). The non-used radiation is absorbed at the walls of diaphragm cavity (85). These walls are completely blackened so that no higher divergent radiation enters the volume of the magnifying glass (77) through mousehole opening (82 or 84). Since the diaphragm (81) absorbs the largest part of the radiation, cooling ribs (86) are provided on the upper side of the diaphragm (81).

Independent of the use in connection with the apparatus for examination of documents, it turned out that the magnifying glass with the tangentially incident grazing light can be very useful for general forensic purposes, such as the display of finger traces on dusty surfaces, fibers, danders and other traces which distinguish only minimally from the base surface.

Figure 9:
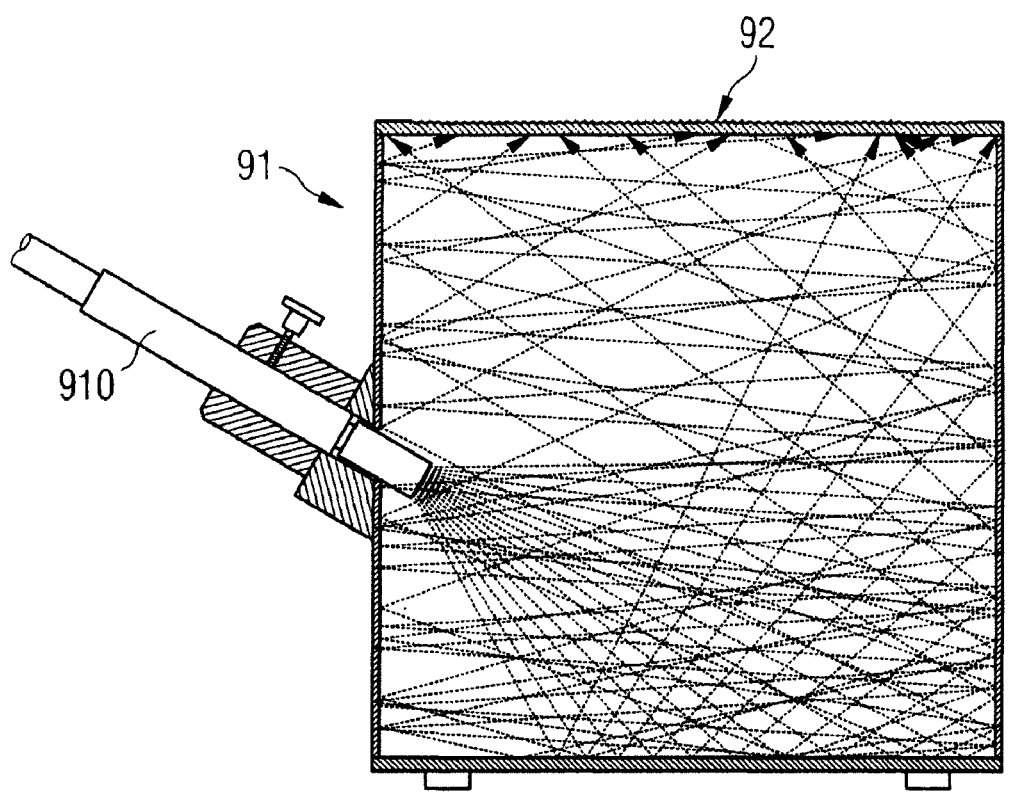
FIG. 9 shows a cross-sectional view of a portion of the first embodiment of FIG. 2 wherein the inner construction of the mirror box has been changed.

FIG. 9 shows a mirror box (91) having highly reflective inner walls and no obliquely disposed mirror panel. A light guide (910) is mounted in the mirror box (91) at an angle of about 45°, so that it is at first illuminating the base plate of the box (91). The radiation undergoes multiple reflection at the side walls and reaches supporting panel (92) which can be transparent or provided with an absorbing or fluorescent dye. This setup effects a particularly homogeneous illumination of the supporting panel (92).

Figure 10:
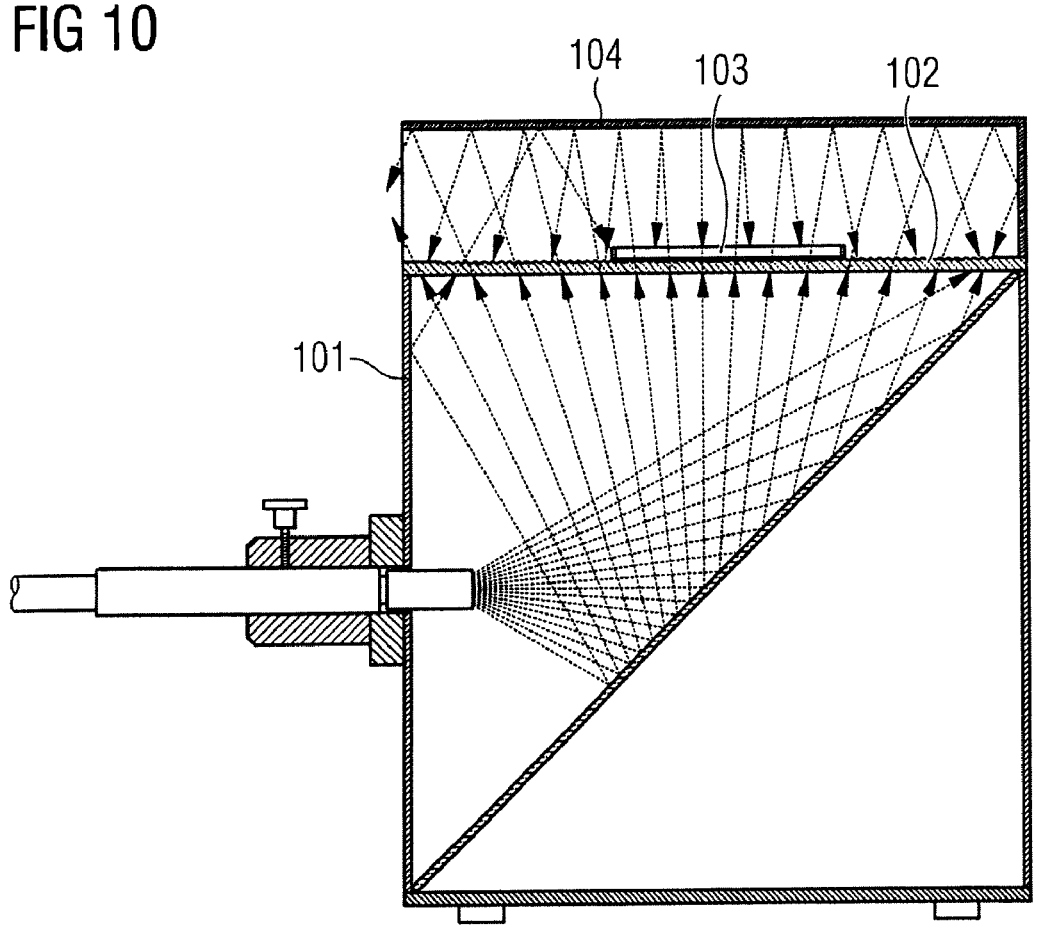
FIG. 10 shows a cross-sectional view of a portion of the first embodiment of FIG. 2, wherein a reflector top is added.

FIG. 10 shows a cross-section of a mirror box (101) with a box-shaped rectangular reflector top (104). The reflector top (104) has walls which are metallized inside and is put onto a supporting panel (102). The reflector top (104) remains open at least one side for input and observation. With this top (104), documents (103) such as passports, can be illuminated simultaneously from above and below in order to recognize internal watermarks or fluorescent markers more readily.

Figure 11:
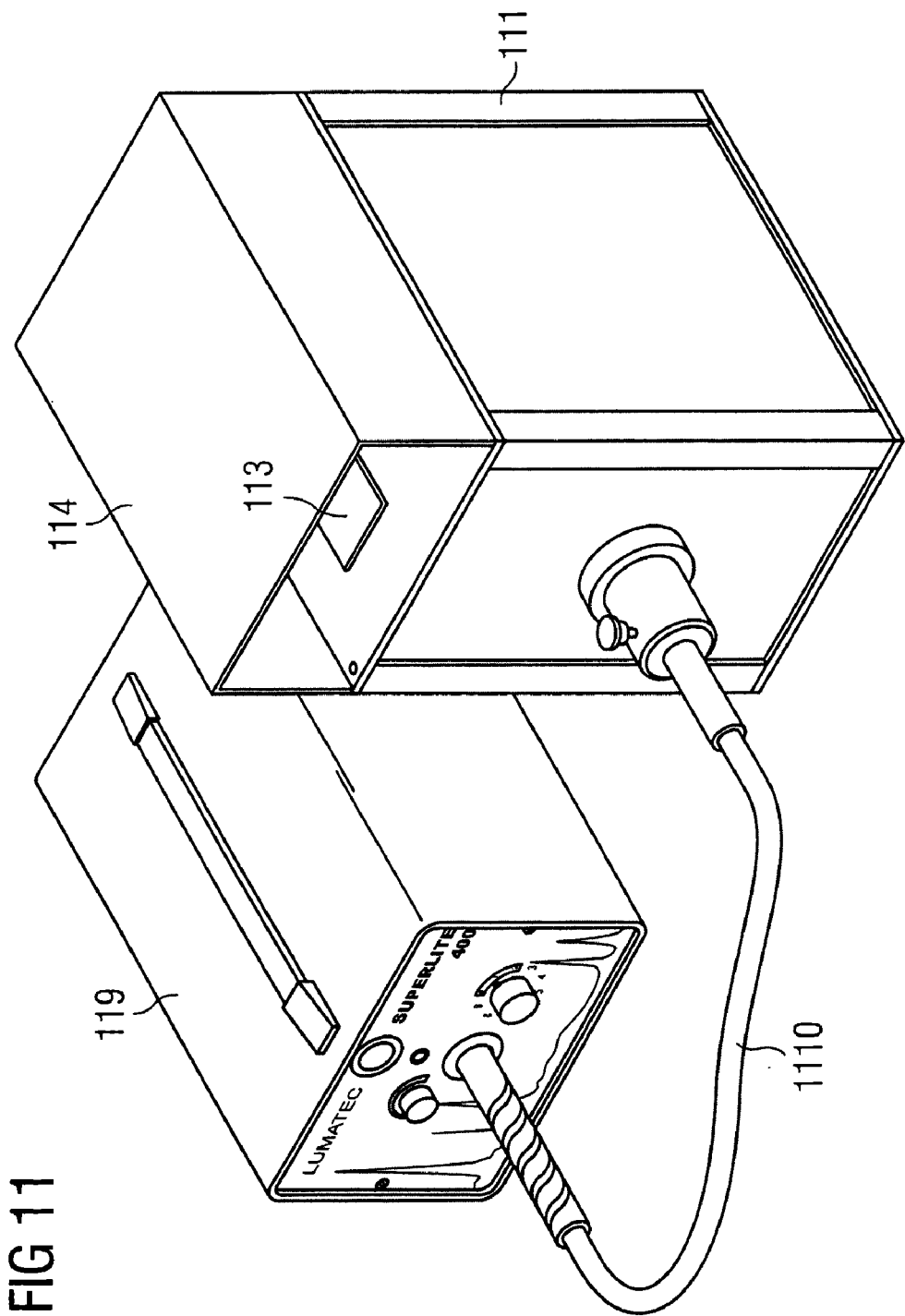
FIG. 11 shows a perspective view of the apparatus for optical examination of documents according to the first embodiment of FIG. 1 and having a reflector top similar to that in FIG. 10.

FIG. 11 shows in total a mirror box (111) having a reflector top (114) for the double-sided viewing of a document (113), such as a personal identity card, etc. The view also shows a liquid light guide (1110) and a light source (119).

Figure 12:
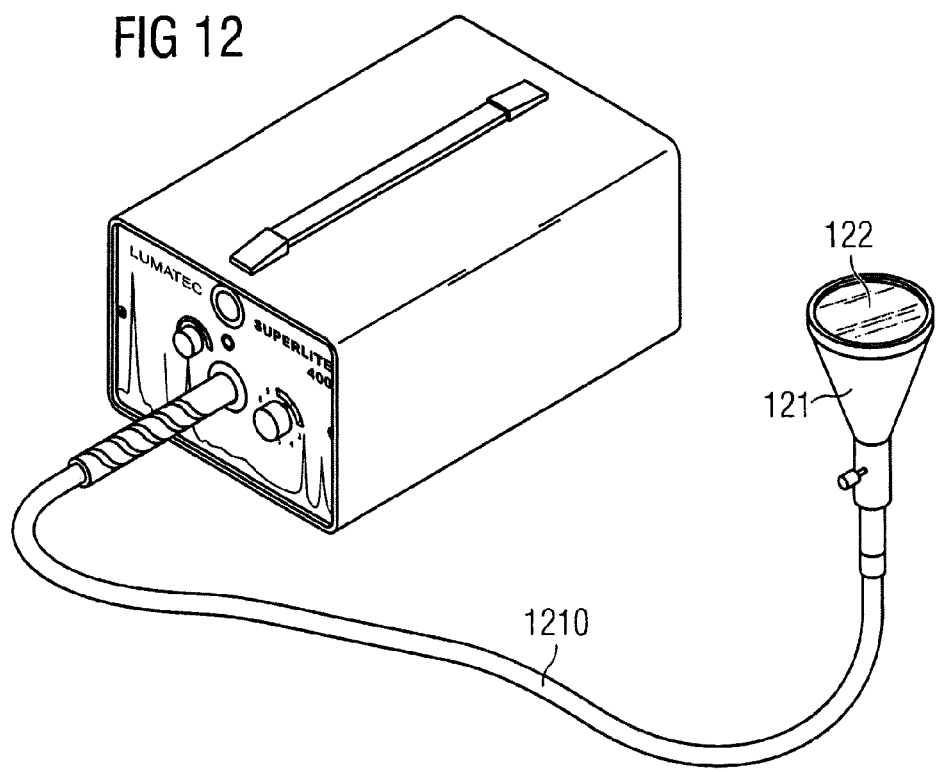
FIG. 12 shows a perspective view of the apparatus for optical examination of documents, according to a fourth embodiment of the present disclosure, showing a viewing unit in the form of a funnel-shaped light output device and a window in the form of a transparent panel.
Figure 13:
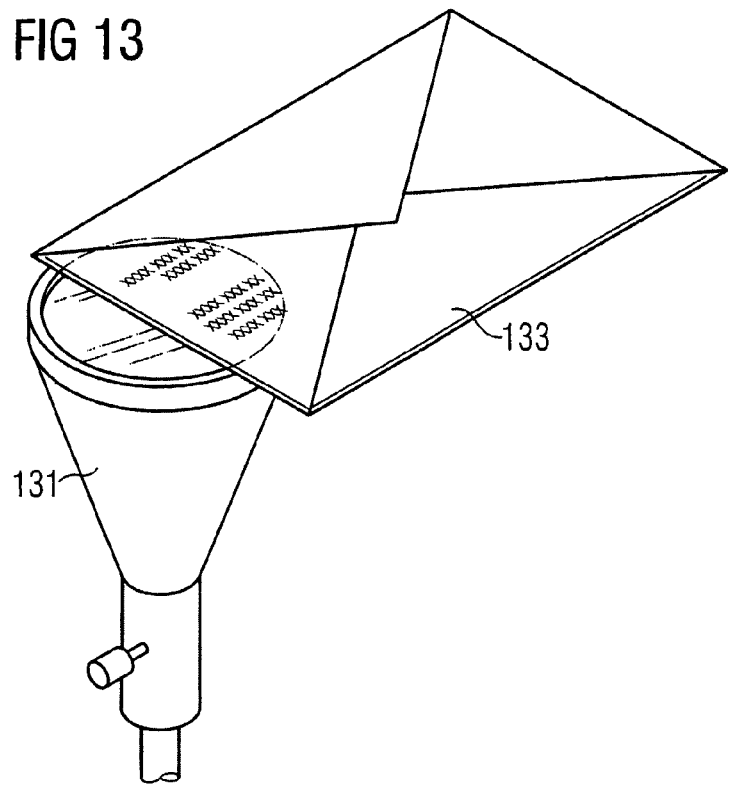
FIG. 13 shows a perspective view of a portion of the light output device of FIG. 12.

FIG. 12 and FIG. 13 show another embodiment, according to the present disclosure, which enables a particularly intensive and flexible light-transmitting unit for quickly checking and sorting documents. As the light output device, a funnel (121) is herein put onto a light output end of a liquid light guide (1210). The open end of the funnel is covered by a plastics or glass panel (122). which may be a supporting panel, which can be transparent or doped with dyes or fluorescent dye substances. The funnel (121) may be metallized inside. The diameter of the supporting panel (122) is only from about 5 to 15 cm, so that the intensity of the emanating light is very high. In order to restrict the aperture effect a bit, it is advisable to use an acrylic glass panel as the panel (122) and to dope it with the perylene dye "Lumogen® red".

FIG. 13 shows a light transmission funnel (131) of this kind during the viewing of a document which is, in this case, a written document inside a closed envelope (133).

Although the present disclosure has been described and illustrated in detail, it is to be clearly understood that this is done by way of illustration and example only and is not to be taken by way of limitation. The scope of the present disclosure is to be limited only by the terms of the appended claims.

The invention claimed is:

1. An apparatus for optical examination of documents, comprising:
   a light source,
   a plurality of panels which are exchangeable with each other,
   a viewing unit having a window formed by at least one of the plurality of exchangeable panels through which window light emitted from the light source exits for examination of documents by an observer;
   a coupling unit configured to supply the light emitted from the light source into the viewing unit;

wherein the light source and the viewing unit are coupled together by a light guide, the light guide being adapted to supply the light from the light source to the coupling unit; and wherein at least one of the plurality of exchangeable panels is a fluorescent panel including a fluorescent substance, such that the fluorescent panel is fluorescent in the yellow-red-infrared wavelength range when being illuminated with light in the ultraviolet-blue-green wavelength range.

2. The apparatus of claim 1, wherein the light guide is a flexible tube having a liquid light guiding core.

3. The apparatus of claim 1, wherein
the coupling unit comprises one or both of a sleeve mounted at a side wall of the viewing unit and a diffusor for widening and homogenizing the light ray, and at least one of the sleeve and the diffusor being arranged at a light output end of the coupling unit.

4. The apparatus of claim 1, wherein the viewing unit is formed by a box including at least one mirror to let the light emitted from the light source through the window to the outside of the box.

5. The apparatus of claim 1, wherein each of the plurality of panels is adapted to support the document under examination in order to be able to transmit the light output from the window through the document in the direction of the observer.

6. The apparatus of claim 5, wherein the fluorescent panel is made of a transparent medium doped with a red, infrared, yellow or orange fluorescent dye.

7. The apparatus of claim 5, wherein an upper side and at least one side edge of the fluorescent panel is metallized, so that the fluorescent panel lets the light exit only horizontally at an at least one non-metallized side edge of the fluorescent panel.

8. The apparatus of claim 1, wherein the fluorescent substance is a fluorescent perylene compound.

9. The apparatus of claim 8, wherein the fluorescent substance is a dye.

10. The apparatus of claim 8, wherein the fluorescent perylene compound is a dye.

* * * * *